United States Patent [19]
Kemper et al.

[11] Patent Number: 6,110,684
[45] Date of Patent: Aug. 29, 2000

[54] MISMATCH DETECTION TECHNIQUES

[75] Inventors: Börries Kemper, Koln; Karin Birkenkamp-Demtröder, Solingen; Stefan Golz, Essen, all of Germany

[73] Assignee: Variagenics, Inc., Cambridge, Mass.

[21] Appl. No.: 09/243,558

[22] Filed: Feb. 2, 1999

Related U.S. Application Data

[60] Provisional application No. 60/073,716, Feb. 4, 1998.

[51] Int. Cl.[7] .............................. C12Q 1/68; C12Q 1/34; C12Q 1/70; C12P 19/34
[52] U.S. Cl. .............................. 435/6; 435/18; 435/91.2; 435/5
[58] Field of Search ........................... 435/5, 6, 18, 91.2

[56] References Cited

U.S. PATENT DOCUMENTS

| | | | |
|---|---|---|---|
| 5,217,863 | 6/1993 | Cotton et al. | 435/6 |
| 5,459,039 | 10/1995 | Modrich et al. | 435/6 |
| 5,571,676 | 11/1996 | Shuber | 435/6 |
| 5,698,400 | 12/1997 | Cotton et al. | 435/6 |
| 5,824,471 | 10/1998 | Mashal et al. | 435/6 |
| 5,851,770 | 12/1998 | Babon et al. | 435/6 |
| 5,876,941 | 3/1999 | Landegren et al. | 435/6 |
| 6,027,898 | 2/2000 | Gjerde et al. | 435/6 |
| B1 4,683,202 | 11/1990 | Mullis | 435/91 |

FOREIGN PATENT DOCUMENTS

| | | |
|---|---|---|
| WO 89/09835 | 10/1989 | WIPO . |
| WO 93/02216 | 2/1993 | WIPO . |
| 97/09434 | 3/1997 | WIPO . |

OTHER PUBLICATIONS

Beck et al., "A denaturing gradient gel electrophoresis assay for sensitive detection of p53 mutations," Hum. Genet. 91:25–30 (1993).

Bhattacharyya et al., "Model for the interaction of DNA junctions and resolving enzymes," J. Mol. Biol. 20:1191–1207 (1991).

Cotton, "Detection of mutations in DNA," Curr. Opin. Biotechnol. 3:24–30 (1992).

Cotton, "Current methods of mutation detection," Mutat. Res. 285:125–144 (1993).

Dahl et al., "Pyruvate dehydrogenase deficiency caused by deletion of a 7–bp repeat sequence in the Elα gene," Am. J. Hum. Genet. 47:286–293 (1990).

DiLella et al., "Screening for phenylketonuria mutations by DNA amplification with the polymerase chain reaction," Lancet 1:497–499 (1988).

Forrest et al., "Use of the chemical cleavage of mismatch method for prenatal diagnosis of alpha–1–antitrypsin deficiency," Prenat. Diagn. 12:133–137 )1992).

Lopez–Galindez et al., "Characterization of genetic variation and 3'–azido–3' deoxythymidine resistance mutations of human immunodeficiency virus by RNase A mismatch cleavage method," Proc. Natl. Acad. Sci. 88:4280–4284 (1991).

Golz et al., "Improved large–scale preparation of phage T4 endonuclease VII overexpressed in *E. coli*," DNA Res. 2:277–284 (1985)., Golz et al., "Enzymatic mutation detection. Procedure for screening and mapping of mutations by immobilised endonuclease VII," Nucleic Acids Res. 26:1132–1133 (1998).

Jensch et al., "Cruciform cutting endonucleases from *Sacchromyces cerevisiae* and phage T4 show conserved reaction with branched DNAs," EMBO J. 8:4325–4334 (1989).

Kemper et al., Resolution of holliday structures of endonuclease VII as observed in interactions with cruciform DNA; Cold Spring Harbor Symp. Quant. Biol. 49:815–825 (1984).

Kleff et al., "Initiation of heteroduplex–loop repair by T4–encoded endonuclease VII in vitro," EMBO J. 7:1527–1535 (1988).

Kosak et al., "Large–scale preparation of T4 endonuclease VII rrom over–expresing bacteria," Eur. J. Biochem. 194:779–784 (1990).

Lilley et al. "Cruciform–resolvase interactions in super-coiled DNA," Cell 36:413–422 (1984).

Lin et al., "Geographical clusters of dengue virus type 2 isolates based on analysis of infected cell RNA by the chemical cleavage at mismatch method," J. Virol. Methods 40:205–218 (1992).

Lu et al., "Detection of single DNA base mutations with mismatch repair enzymes," Genomics 14:249–255 (1992).

Mizuuchi et al., "T4 endonuclease VII cleaves holliday structures," Cell 29:357–365 (1982).

Mueller et al., "T4 endonuclease VII cleaves the crossover strands of holliday junction analogs," Proc. Natl. Acad. Sci. USA 85:9441–9445 (1988).

Müller et al., "Enzymatic formation and resolution of holliday junctions in vitro," Cell 60:329–336 (1990).

Parsons et al., "Resolution of model holliday junctions by yeast endonuclease is dependent upon homologous DNA sequences," Cell 52:621–629 (1988).

Parsons et al., "Interaction of a four–way junction in DNA with T4 endonucleas VII," J. Biol. Chem. 265:9285–9289 (1990).

(List continued on next page.)

*Primary Examiner*—Carla J. Myers
*Assistant Examiner*—Diana Johannsen
*Attorney, Agent, or Firm*—Clark & Elbing LLP

[57] ABSTRACT

Disclosed herein is a method for detecting a mismatch in a duplex nucleic acid, involving: a) contacting the duplex nucleic acid with a reactive agent under conditions which permit the agent to bind but not cleave a mismatch in said duplex nucleic acid; b) detecting binding of the agent to the duplex nucleic acid as an indication of the presence of a mismatch in the duplex nucleic acid; c) contacting the duplex nucleic acid with the reactive agent under conditions which permit the agent to cleave a mismatch in the duplex nucleic acid; and d) detecting a cleavage product as an indication of the presence of a mismatch in the duplex nucleic acid.

50 Claims, 3 Drawing Sheets

OTHER PUBLICATIONS

Pottmeyer et al., "T4 endonuclease VII resolves cruciform DNA with nick and counter–nick and its activity is directed by local nucleotide sequence," J. Mol. Biol. 223:607–615 (1992).

Shenk et al., "Biochemical method for mapping mutational alterations in DNA with S1 nuclease:The location of deletions and temperature–sensitive mutations in simian virus 40*," Proc. Nat. Acad. Sci. 72:989–993 (1975).

Smooker et al., "Identification and in vitro expression of mutations causing dihydropteridine reductase deficiency," Biochemistry 32:6443–6449 (1993).

Solaro et al., "Endonuclease VII of phage T4 triggers mismatch correction in vitro," J. Mol. Biol. 230:868–877 (1993).

Telenti et al., "Detection of rifampicin–resistance mutations in *Mycobacterium tuberculosis*," Lancet 341:647–650 (1993).

West, "Enzymes and molecular mechanisms of genetic recombination," Annu. Rev. Biochem. 61:603–640 (1992).

Winter et al., "A method to detect and characterize point mutations in transcribed genes: Amplification and overexpression of the mutant c–Ki–ras allele in human tumor cells," Proc. Natl. Acad. Sci. USA 82:7575–7579 (1985).

Youil et al., "Screening for mutations by enzyme cleavage of mismatch using T4 endonuclease VII," The American Society of Human Genetics 53:1257 (1993).

Youil et al., "Detection of 81 of 81 known mouse β–globin promoter mutations with T4 endonuclease VII—The EMC method," Genomics 32:431–435 (1996).

1

MISMATCH DETECTION TECHNIQUES

BACKGROUND OF THE INVENTION

This application claims benefit from co-pending provisional application, U.S. Ser. No. 60/073,716, filed Feb. 4, 1998.

In general, this invention relates to mismatch detection techniques.

The ability to detect mismatches in coding and non-coding DNA, as well as RNA, is important in a number of diagnostic as well as therapeutic contexts. Such a mismatch may occur at a single nucleotide or over multiple nucleotides, and may result from a frame shift, stop codon, or substitution in a gene, each of which can independently render an encoded protein inactive. Alternatively, the mismatch may indicate a genetic variant which is harmless, resulting in a protein product with no detectable change in function (for example, a harmless gene polymorphism). Eight single base mismatches are possible, and these include G:A, C:T, C:C, G:G, A:A, T:T, C:A, and G:T, with U being substituted for T when the nucleic acid strand is RNA. Nucleic acid loops can form when at least one strand of a mismatch-containing sequence, or heteroduplex, includes a deletion, substitution, insertion, transposition, or inversion of DNA or RNA.

In one particular application, mismatch detection techniques may be used for identifying or evaluating mutations in nucleic acid sequences. Mutations are heritable changes in the sequence of the genetic material of an organism which can cause fatal defects like hereditary diseases or cancer (recent reviews in Modrich, Science 266: 1959–1960 (1994)). As a result, methods for mutation detection are gaining increasing importance especially in medical diagnostics. Although mutations can be localized with great precision by DNA sequencing (Sanger et al. Proc. Natl. Acad. Sci. USA 74: 5463– 5467 (1977)), this procedure is relatively time consuming and expensive, and requires toxic chemicals. Alternatively, procedures have been developed that measure mutations by mispairings in heteroduplex DNAs obtained after annealing wild-type with mutant sequences in vitro (reviewed in Cotton, Mutations Research 285: 125–144 (1993)).

Besides physical and chemical methods, enzymatic assay systems using proteins involved in DNA repair have also been established. One of these enzymes is endonuclease VII of bacteriophage T4 (T4 Endo VII) (Golz et al., DNA Res. 2: 277–284 (1995); Kemper et al., Eur. J. Biochem. 115: 123–131 (1981)). T4 Endo VII assays detect all possible mismatches including C/C mismatches, heteroduplex loops, single nucleotide bulges, single-strand overhangs, branched DNAs, bulky adducts, psoralen crosslinks, and apurinic sites (Kemper, In Nickoloff, J. A. and Hoekstra, M. (eds.), DNA Damage and Repair. Biochemistry, Genetics and Cell Biology, Humana Press, Totowa, Vol. 1 (1997)). The broad substrate specificity makes the enzyme an extremely versatile tool for mismatch detection (Cotton, Mutation detection, Oxford University Press, Oxford (1997)). The nucleolytic activity of T4 Endo VII has been used successfully to detect mutations in heteroduplex DNA by cleavage assays (Youil et al., Genomics 32: 431–435 (1996)).

T4 Endo VII belongs to a class of enzymes termed resolvases, which are characterized by their ability to catalyze the resolution of branched DNA intermediates (e.g., DNA cruciforms), structures which can involve hundreds of nucleotides. Besides T4 Endo VII, the resolvases include, without limitation, bacteriophage T7 Endonuclease I (West, Ann. Rev. Biochem. 61, 603, (1992)) and eukaryotic resolvases, particularly from the yeast *Saccharomyces cerevisiae,* which have been shown to recognize and cleave cruciform DNA (West, supra; Jensch, et al., EMBO J. 8, 4325 (1989)).

SUMMARY OF THE INVENTION

In general, the invention features a method for detecting a mismatch in a duplex nucleic acid, involving: a) contacting the duplex nucleic acid with a resolvase which is capable of cleaving a mismatch in a duplex nucleic acid, under conditions which permit the resolvase to bind but not cleave the mismatch; and b) detecting the resolvase binding to the duplex nucleic acid as an indication of the presence of a mismatch in the duplex nucleic acid.

In preferred embodiments, the resolvase is a bacteriophage or a eukaryotic resolvase (for example, T4 Endonuclease VII); the contacting conditions involve the absence of magnesium; the duplex nucleic acid is labeled with at least one detection moiety either prior to the contact with the resolvase or between the contact with the resolvase and the detection step; the detection moiety is any one of a radioactive label, a fluorescent label, biotin, digoxygenin, a luminescent agent, a dye, or an enzyme; at least one strand of the duplex is labeled with biotin and the detecting step involves reaction of the duplex with a streptavidin-bound detection moiety (for example, an enzyme which produces a detectable color upon reaction with a chromogenic substrate); at least one strand of the duplex nucleic acid is provided by amplification; the resolvase or the duplex nucleic acid is bound to a solid support; the resolvase is bound to the solid support; the solid support is a microtiter plate or a magnetic bead; the contacting step is carried out in solution; the site of resolvase binding is determined; the method further involves the steps of: c) contacting the duplex nucleic acid with the resolvase under conditions which permit the resolvase to cleave a mismatch in the duplex nucleic acid; and d) detecting a cleavage product as an indication of the presence of a mismatch in the duplex nucleic acid; the resolvase cleaves at or within 10 nucleotides (and, preferably, within 6 nucleotides) of the mismatch; the site of the resolvase cleavage reaction is determined; the duplex nucleic acid is obtained from a heterozygote; at least one strand of the duplex nucleic acid is derived from a eukaryotic cell, a eubacterial cell, a bacterial cell, a mycobacterial cell, a bacteriophage, a DNA virus, or an RNA virus; at least one strand of the duplex nucleic acid is derived from a human cell; the duplex nucleic acid comprises at least one strand having a wild-type sequence; the mismatch indicates the presence of a mutation; the mutation is diagnostic of a disease or condition; the mismatch indicates the presence of a polymorphism; and the mismatch occurs in an essential gene.

In a related aspect, the invention features a method for detecting a mismatch in a duplex nucleic acid, involving: a) contacting the duplex nucleic acid with a reactive agent under conditions which permit the agent to bind but not cleave a mismatch in the duplex nucleic acid; b) detecting binding of the agent to the duplex nucleic acid as an indication of the presence of a mismatch in the duplex nucleic acid; c) contacting the duplex nucleic acid with the reactive agent under conditions which permit the agent to cleave a mismatch in the duplex nucleic acid; and d) detecting a cleavage product as an indication of the presence of a mismatch in the duplex nucleic acid.

In preferred embodiments, the binding reaction and the cleaving reaction are carried out on the same sample; the binding reaction and the cleaving reaction are carried out on separate samples of the same duplex nucleic acid (in any order or simultaneously); the reactive agent is T4 Endonuclease VII; the binding reaction conditions involve the absence of magnesium and the cleaving reaction conditions involve the presence of magnesium; the duplex nucleic acid is labeled with at least one detection moiety either prior to the contact with the reactive agent or between the contact with the reactive agent and the detection step (b) or (d); the detection moiety is any one of a radioactive label, a fluorescent label, biotin, digoxygenin, a luminescent agent, a dye, or an enzyme; at least one strand of the duplex is labeled with biotin and the detecting step involves reaction of the duplex with a streptavidin-bound detection moiety (for example, an enzyme which produces a detectable color upon reaction with a chromogenic substrate); at least one strand of the duplex nucleic acid is provided by amplification; the reactive agent is bound to a solid support during the detecting step (b); the solid support is a microtiter plate or a magnetic bead; the binding reaction, the cleaving reaction, or both is carried out in solution; the site of the mismatch is determined in step (b), step (d), or both; the reactive agent cleaves at or within 10 nucleotides (and, preferably, within 6 nucleotides) of the mismatch; the duplex nucleic acid is obtained from a heterozygote; at least one strand of the duplex nucleic acid is derived from a eukaryotic cell, a eubacterial cell, a bacterial cell, a mycobacterial cell, a bacteriophage, a DNA virus, or an RNA virus; at least one strand of the duplex nucleic acid is derived from a human cell; the duplex nucleic acid includes at least one strand having a wild-type sequence; the mismatch indicates the presence of a mutation; the mutation is diagnostic of a disease or condition; the mismatch indicates the presence of a polymorphism; and the mismatch occurs in an essential gene.

As used herein, the term "mismatch" means that a nucleotide in one strand of DNA or RNA does not or cannot pair through Watson-Crick base pairing and π-stacking interactions with a nucleotide in an opposing complementary DNA or RNA strand. Thus, adenine in one strand of DNA or RNA would form a mismatch with adenine in an opposing complementary DNA or RNA strand. Mismatches also occur where a first nucleotide cannot pair with a second nucleotide in an opposing complementary DNA or RNA strand because the second nucleotide is absent (i.e., one or more nucleotides are inserted or deleted). The methods of the invention are especially useful in detecting a mismatch in a test nucleic acid which contains between 1 and 50 (preferably, between 1 and 10 and, more preferably, between 1 and 7) nucleotide sequence changes (inclusive).

As used herein, a "resolvase" is any protein capable of recognizing and cleaving a cruciform DNA as well as any mismatch (for example, a mismatch loop) in a heteroduplex template. Examples of resolvases include, without limitation, T4 endonuclease VII, Saccharomyces cerevisiae Endo X1, Endo X2, Endo X3, and CCE1 (Jensch et al., EMBO J. 8:4325, 1989; Kupfer and Kemper, Eur. J. Biochem. 238:77, 1995), T7 endonuclease I, *E. coli* MutY (Wu et al., Proc. Natl. Acad. Sci. USA 89:8779–8783, 1992), mammalian thymine glycosylase (Wiebauer et al., Proc. Natl. Acad. Sci. USA 87:5842–5845, 1990), topoisomerase I from human thymus (Yeh et al., J. Biol. Chem. 266:6480–6484, 1991; Yeh et al., J. Biol. Chem. 269:15498–15504, 1994), and deoxyinosine 3' endonuclease (Yao and Kow, J. Biol. Chem. 269:31390–31396, 1994). In a given mismatch detection assay, one or several resolvases may be utilized.

A "mutation," as used herein, refers to a nucleotide sequence change (i.e., a single or multiple nucleotide substitution, deletion, or insertion) in a nucleic acid sequence that produces a phenotypic result. A nucleotide sequence change that does not produce a detectable phenotypic result is referred to herein as a "polymorphism."

By an "essential gene" is meant a gene whose product is necessary for cell viability.

By a "reactive agent" is meant any molecule (including a protein, peptide, or other organic molecule) that carries out both a binding and a cleaving reaction, but under different reaction conditions.

By the term "heteroduplex" is meant a structure formed between two annealed, complementary nucleic acid strands (e.g., the annealed strands of test and reference nucleic acids) in which one or more nucleotides in the first strand are unable to appropriately base pair with those in the second opposing, complementary strand because of one or more mismatches. Examples of different types of heteroduplexes include those which exhibit an exchange of one or several nucleotides, and insertion or deletion mutations, each of which is disclosed in Bhattacharyya and Lilley, Nudl. Acids. Res. 17: 6821 (1989). The term "complementary," as used herein, means that two nucleic acids, e.g., DNA or RNA, contain a series of consecutive nucleotides which are capable of forming matched Watson-Crick base pairs to produce a region of double-strandedness. Thus, adenine in one strand of DNA or RNA pairs with thymine in an opposing complementary DNA strand or with uracil in an opposing complementary RNA strand. The region of pairing is referred to as a "duplex." A duplex may be either a homoduplex or a heteroduplex.

As used herein, the phrase "preferentially hybridizes" refers to a nucleic acid strand which anneals to and forms a stable duplex, either a homoduplex or a heteroduplex, under normal hybridization conditions with a second complementary nucleic acid strand, and which does not form a stable duplex with unrelated nucleic acid molecules under the same normal hybridization conditions. The formation of a duplex is accomplished by annealing two complementary nucleic acid strands in a hybridization reaction. The hybridization reaction can be made to be highly specific by adjustment of the hybridization conditions (often referred to as hybridization stringency) under which the hybridization reaction takes place, such that hybridization between two nucleic acid strands will not form a stable duplex, e.g., a duplex that retains a region of doublestrandedness under normal stringency conditions, unless the two nucleic acid strands contain a certain number of nucleotides in specific sequences which are substantially or completely complementary. "Normal hybridization or normal stringency conditions" are readily determined for any given hybridization reaction (see, for example, Ausubel et al., *Current Protocols in Molecular Biology,* John Wiley & Sons, Inc., New York, or Sambrook et al., *Molecular Cloning: A Laboratory Manual,* Cold Spring Harbor Laboratory Press).

By "specific binding pair" is meant any pair of molecules, including a first and a second member, which have a specific, covalent or noncovalent affinity for each other. Examples of specific binding pairs include antigen/antibody pairs, DNA binding protein/DNA binding site pairs, enzyme/substrate pairs, lectin/carbohydrate pairs, and nucleic acid duplexes or ligated DNA strands. A preferred specific binding pair of the invention is avidin (for example, streptavidin) and biotin.

A "reference nucleic acid," as used herein, is any sequence of DNA or RNA that is at least 20 nucleotides in length, preferably between 100 and 40,000 nucleotides in length, and more preferably between 150 and 5000 nucleotides in length. Often, the reference nucleic acid will have a sequence that is indistinguishable from DNA obtained from a corresponding wild-type population.

A "test nucleic acid" is any sequence of DNA or RNA that is at least 20 nucleotides in length, preferably between 100 and 40,000 nucleotides in length, and more preferably between 150 and 5000 nucleotides in length. When particularly large test nucleic acid fragments are analyzed (i.e., larger than 2 kb), the nucleic acid may be cleaved with a second restriction enzyme in order to obtain a fragment of a size suitable for denaturing polyacrylamide gel electrophoresis (<2 kb). The choice of a second restriction enzyme will be guided by creating a restriction enzyme map of the DNA fragment.

If desired, the test or reference nucleic acids may be isolated prior to carrying out the detection assay. By an "isolated nucleic acid" is meant a nucleic acid segment or fragment which is not immediately contiguous with (i.e., covalently linked to) both of the nucleic acids with which it is immediately contiguous in the naturally occurring genome of the organism from which the nucleic acid is derived. The term, therefore, includes, for example, a nucleic acid which is incorporated into a vector, for example, a bacteriophage, virus, or plasmid vector capable of autonomous replication. The term "isolated nucleic acid" may also include a nucleic acid which is substantially purified from other nucleic acids, such as a nucleic acid fragment produced by chemical means, selective amplification, or restriction endonuclease treatment. Because the detection assays of the invention may be used to simultaneously analyze more than one DNA sequence, isolation and purification are not required, but may be carried out if desired.

As disclosed in more detail below, the present invention provides a simple and inexpensive means for detecting DNA mismatches in nucleic acid samples. The rapid and sensitive nature of the claimed methods and their ability to be readily automated renders them practical for large scale screening of multiple samples or for screening a particular sample against a number of reference nucleic acids. The binding assay, for example, may be facilitated by the use of pre-produced microtiter plates coated with a particular reactive agent (such as T4 Endo VII), which can be stored with refrigeration for extended periods of time and the results of which may be processed by robotics. In addition, the use of a reactive agent that, simply by a change in reaction conditions, can be utilized in both a very rapid binding assay and a second, cleavage-based assay provides advantages over more conventional techniques, particularly in terms of cost and sensitivity. Importantly, this latter approach allows for a double check on the mismatch detection step, and also allows mass screening by means of a simple and inexpensive binding assay followed by the ability to determine the mismatch site by means of a precise cleaving assay.

The techniques described herein are extremely useful for detecting DNA mutations and polymorphisms associated with mammalian diseases (such as cancer and various inherited diseases), as well as mutations which facilitate the development of therapeutics for their treatment. Alternatively, the methods are also useful for forensic applications or the identification of useful traits in commercial (for example, agricultural) species.

Those skilled in the art will recognize that the invention is also useful for other purposes. For example, the claimed method facilitates detection of single base pair mismatches in cloned DNA, for example, mutations introduced during experimental manipulations (e.g., transformation, mutagenesis, PCR amplification, or after prolonged storage or freeze:thaw cycles). This method is therefore useful for testing genetic constructs that express therapeutic proteins or that are introduced into a patient for gene therapy purposes.

The method may also be used for rapid typing of bacterial and viral strains. By "type" is meant to characterize an isogeneic bacterial or viral strain by detecting one or more nucleic acid mutations that distinguishes the particular strain from other strains of the same or related bacteria or virus. As an example, genetic variation of the human immunodeficiency virus has led to the isolation of distinct HIV types, each bearing distinguishing gene mutations (Lopez-Galindez et al., Proc. Natl. Acad. Sci. USA 88:4280 (1991)). Other examples of test DNAs of particular interest for typing include test DNAs isolated from viruses of the family Retroviridae, for example, the human T-lymphocyte viruses or human immunodeficiency viruses (in particular, any one of HTLV-I, HTLV-II, HIV-1, or HIV-2), DNA viruses of the family Adenoviridae, Papovaviridae, or Herpetoviridae, bacteria, or other organisms, for example, organisms of the order Spirochaetales, of the genus Treponema or Borrelia, of the order Kinetoplastida, of the species *Trypanosoma cruzi*, of the order Actinomycetales, of the family Mycobacteriaceae, of the species *Mycobacterium tuberculosis*, or of the genus Streptococcus.

Unless otherwise defined, all technical terms and scientific terms used herein have the same meaning as commonly understood by one of ordinary skill in the art to which this invention belongs. All publications mentioned herein are incorporated by reference.

Other features and advantages of the invention will be apparent from the following description of the detailed description and from the claims.

DETAILED DESCRIPTION OF THE INVENTION

The drawings will first briefly be described.

DESCRIPTION OF THE DRAWINGS

FIG. 1A shows results using PCR fragments of 84 nucleotides and 164 nucleotides having each possible mismatch centrally located in the fragment sequence. For hybridization, equal amounts of mutant and wild-type PCR fragments were mixed in 100 pl TE-buffer (10 mM Tris-HCl pH 8.0, 1 mM EDTA). The hybridization was performed in a Biometra thermocycler by stepwise cooling of the sample in 10° C. steps (15 minutes per step), beginning with an initial 5 minute denaturing step at 95° C. After hybridization, the DNA was 5'-end labeled by standard methods. FIG. 1B shows results using heteroduplexes formed from PCR fragments of 263 nucleotides in length and having either centrally located C/C and G/G mismatches or a centrally located 8 nucleotide insertion. Binding to immobilized T4 Endo VII and assay of the amount of bound materials was done in the same way as described for FIG. 1A above. FIG. 1C shows results demonstrating the sensitivity of the binding assay as tested by mixing equal amounts of synthetic heteroduplex substrates having a C/C mismatch ("MMCC") or an 8 nucleotide insert "8nt-loop") with different amounts of homoduplex DNA, each at its individual optimal concentration of phosphate buffer. Assays were carried out according to the protocol described in FIG. 1A. For FIGS. 1A–1C, "ctr" indicates controls containing hybrid homoduplexes without mispairings, and "std" indicates standards containing labeled substrate, at 15,000 psi per spot.

FIG. 2A shows results from simultaneous addition of T4 Endo VII and heteroduplex DNA to the wells of the microtiter plates. FIG. 2B shows results from successive addition of T4 Endo VII and heteroduplex DNA to the wells of the microtiter plates. In both experiments the same series of phosphate-buffer ("P") concentrations (in mM) were used, that is P20, P50, P100, and P150, as indicated above the blots. Aliquots taken from the material retained in the wells after extensive washings were spotted on filter papers and quantitated by phosphorimaging. Sample images are shown. In FIGS. 2A and 2B, "std" indicates standards containing the total amount of input DNA; "8nt" indicates heteroduplex DNA with an insertion loop of 8 nucleotides; "CFM13" indicates synthetic branched cruciform DNA; "MMCC" indicates heteroduplex hairpin DNA with a centrally located C/C mismatch (complete sequence shown in FIG. 2E); and "control" indicates homoduplex hairpin DNA. FIG. 2C shows a comparison of relative binding efficiencies for different substrates as measured by protocol II (and as shown in FIG. 2B). In FIG. 2C, the light gray bars correspond to the "8nt" samples, the black bars correspond to the "CFM13" samples, the white bars correspond to the "MMCC" samples, and the dark gray bars correspond to the "control" samples. FIG. 2D indicates the nucleotide sequence of the hairpin substrate MMCC (SEQ. ID. NO: 1). Arrows point to the T4 Endo VII cleavage sites mapped in the experiments shown in FIG. 2E. FIG. 2E shows that the nuclease activity of T4 Endo VII was activated in an aliquot taken from well "MMCC/P100" (from FIG. 2B) by the addition of 1 5mM $Mg^{2+}$. The products of the reaction were separated on a 10% denaturing PAA gel. Cleavages flanking mismatch C/C in 5' end-labeled substrate "MMCC" (shown in FIG. 2D) produced fragments of 36 nucleotides and 15 nucleotides in length. In FIG. 2E, lane 1 shows control DNA, and lane 2 shows MMCC DNA.

Figure 1A:
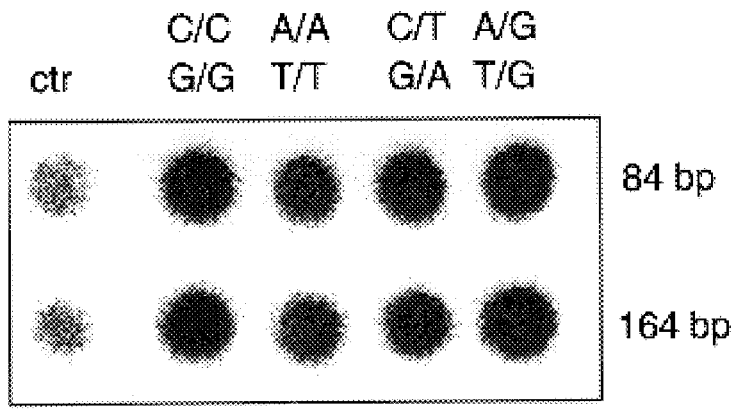
FIGS. 1A–1C are photographs illustrating the selective binding of heteroduplex DNA by immobilized T4 Endo VII. Binding of heteroduplex DNA to immobilized T4 Endo VII was tested by adding 5'-end labeled heteroduplex DNAs to T4 Endo VII-coated wells of microtiter plates in 75 mM phosphate buffer (pH 6.5) as described herein. Following removal of excess DNA by extensive washings, the amount of bound DNA was determined by spotting an aliquot of the sample recovered from the well to filter paper. The amount of radioactivity was determined by phosphor-imaging. Images of samples are shown.

Described below is an improved method that is based on the binding of mismatches and bulges in heteroduplex DNAs by immobilized T4 Endo VII in the absence of $Mg^{2+}$. The use of microtiter plates allows screening of large numbers of samples, making the procedure fast, easy, and versatile. Mutations in the heteroduplex may be determined at this binding step or may be assayed by T4 Endo VII cleavage following incubation of aliquots of positive binding samples in the presence of $Mg^{2+}$ (Solaro et al., J.Mol. Biol. 230: 868–877 (1993); Youil et al., Proc. Natl. Acad. Sci. USA 92: 87–91 (1995)). A combination of a binding step and a cleavage step, using a single resolvase reagent, provides the ability to screen large numbers of unknown samples in a microtiter format, further processing only the positive samples while eliminating the majority of samples (i.e., the negative samples).

Detection of Mismatches by Resolvase Binding

A T4 Endo VII binding assay was tested for all possible mismatches centrally located in heteroduplex DNAs of 84bp and 164bp annealed from gel purified, PCR-amplified strands. Heteroduplexes of 263bp with a centrally located C/C mismatch or an 8nt-insertion made by the same procedure were also tested.

For coating wells of microtiter plates, highly purified T4 Endo VII (Golz et al., 1995, supra) was diluted to a final concentration of 20 Fg/ml in Phosphate-buffer containing 75mM potassium phosphate buffer (pH 6.5) and 5mM EDTA. Phosphate-buffer was used at pH 6.5 because the cloned enzyme showed considerably higher specific activity in this buffer under certain experimental conditions. In a standard reaction procedure, 1 µg of T4 Endo VII was added in 50 µl to each well of a 96-well microtiter plate and incubated at room temperature for at least 30 minutes or 1 hour. Longer incubation times did not influence the results. The plates could be used immediately or stored in a humid atmosphere at 4° C. for up to seven days without loss of activity. The protein-containing coating solution was not removed from the wells, and sample DNA was added directly.

For the binding assay, approximately 3 finoles of radioactively labeled heteroduplex DNA were added to each well containing protein solution, the microtiter plates were mixed gently, and then incubated for 2 hours in a humid atmosphere at room temperature. Liquid was discarded, and unbound DNA and protein were removed by washing the plates five times each with 200 µl of incubation buffer per well. For the release of bound DNA from the wells, 50 µl of 1% SDS solution was added. Repeated pipetting ensured complete removal. For visualization and documentation, the sample volume was kept small and reduced by vaporization if necessary. 5–10 µl of liquid was spotted onto small Whatman 3MM filters, air dried, and quantitated with a phosphorimager (FujiBas 1000). Yes-or-no answers reported the presence or absence of mutations, and large screens of heteroduplex samples could be processed in less than a few hours.

Figure 1B:
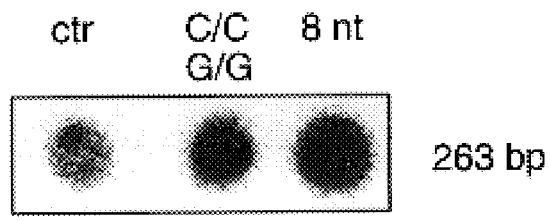
Figure 1C:
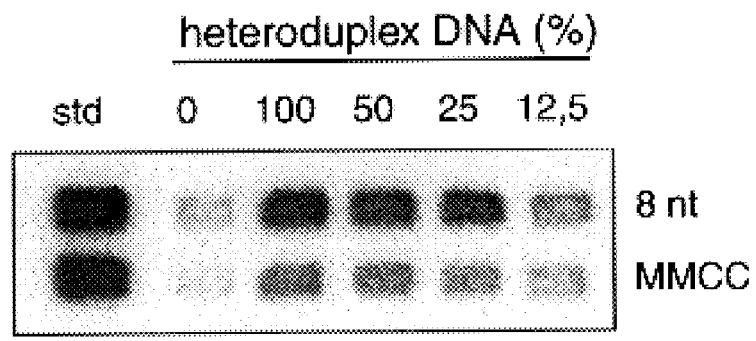

As shown in FIGS. 1A–1C, all mismatches were clearly detected. Differences among individual mismatches were also recognized. The affinity of T4 Endo VII to a mixture of C/C and G/G mismatches was the highest, and to a mixture of A/A and T/T mismatches the lowest. To determine the signal-to-noise ratios for different heteroduplexes, data from repeated binding experiments using heteroduplex PCR-made DNAs of 84bp, 1 64bp and 263bp with all possible mismatches and an 8nt insert were compared. As shown in Table 1, the signal-to-noise ratio between mismatch and control was in all cases better than two (Table 1).

TABLE 1

| Substrate | Experiments (no.) | Signal-to-noise (-fold) | Standard Deviation |
|---|---|---|---|
| PCR-84 bp | | | |
| C/C + G/G | 5 | 3.54 | 0.14 |
| A/A + T/T | 5 | 2.32 | 0.13 |
| C/T + A/G | 5 | 2.64 | 0.16 |
| A/G + C/T | 5 | 3.2 | 0.17 |
| PCR-164 bp | | | |
| C/C + G/G | 5 | 3.46 | 0.25 |
| A/A + T/T | 5 | 2.3 | 0.21 |

TABLE 1-continued

| Substrate | Experiments (no.) | Signal-to-noise (-fold) | Standard Deviation |
|---|---|---|---|
| C/T + A/G | 5 | 2.66 | 0.15 |
| A/G + C/T PCR-263 bp | 5 | 2.98 | 0.21 |
| C/G + G/G | 4 | 3.33 | 0.33 |
| 8nt insert | 4 | 4.9 | 0.16 |

The data presented in FIG. 1C further demonstrated that the sensitivity of the procedure was high, with heteroduplex DNA being detected reliably even at a background of up to 87.5% of homoduplex 'wild-type' DNA. This was tested using synthetic oligonucleotides, one of 44 bp with a C/C mismatch ("MMCC") and the other having an 8 nucleotide insert ("8nt-insert") (FIG. 1C) (Solaro et al., supra). This sensitivity is sufficient for most applications. For example, if PCR-products were obtained from heterozygous cells, 50% of the DNA would be heteroduplex and 50% homoduplex after melting and reannealing. The heteroduplex DNA would contain two complementary mismatches, each representing 25% of the total DNA. In the situation where the enzyme reacted poorly with one of the mismatching nucleotides, sensitivity would still be high due to the availability of the other. Cases in which both mismatches would be detected poorly would be quite rare.

Our results in sensitivity experiments also indicated that the concentration of the phosphate buffer could markedly influence the signal-to-noise ratio for individual heteroduplexes. Concentrations ranging from 20 mM to 150 mM were successfully used in trial experiments with several substrates.

In conclusion, the above experiments demonstrated that, in addition to the ability of T4 Endo VII to cleave at mismatches, its binding ability may also be used for mismatch detection. A similar procedure using immobilized repair protein MutS of *E. coli* was recently reported. However, MutS is not reliable in reporting C/C mismatches, nor does it recognize insertion or deletion mutations (Wagner et al., Nucleic. Acids. Res. 23: 3944–3948 (1995)). In addition, MutS cannot be utilized for simple, second-round cleavage reactions, as demonstrated for Endo VII.

Comparison of Experimental Protocols for Mismatch Detection by T4 Endo VII Binding The binding of heteroduplex DNA by immobilized T4 Endo VII was tested with three different substrates and a control DNA. These DNAs included a linear heteroduplex of 46bp with a centrally located insert of 8 nucleotides ("8nt" in FIGS. 2A–2E), a cruciform DNA ("CFM113" in FIGS. 2A–2E), a heteroduplex hairpin with a C/C mismatch ("MMCC" in FIGS. 2A–2E), and a linear homoduplex with the same sequence but without the mismatch as a control substrate ("control" in FIGS. 2A–2E).

In addition, two different protocols were utilized. Protocol 1 allowed for the binding reaction between T4 Endo VII and the DNA to proceed before the total protein was trapped to the inner surfaces of the wells of microtiter plates. Protocol II started with protein-coated microtiter plates followed by the binding of DNA in a second reaction. In both protocols, the same procedure was used to determine the relative binding strength between bound DNA and T4 Endo VII by applying a series of washes with phosphate buffers of increasing ionic strength and quantitation of the eluted material.

Figure 2A:
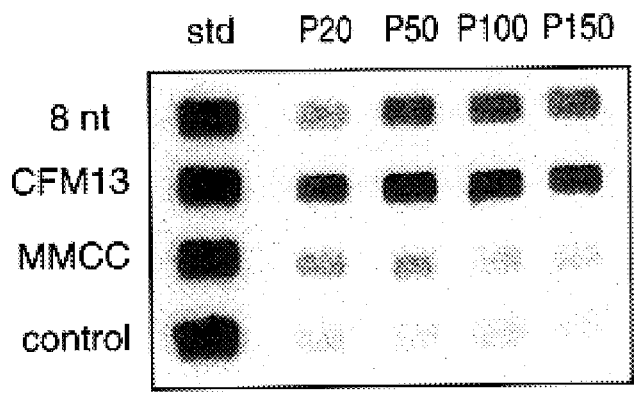
FIGS. 2A–2E demonstrate selective binding of heteroduplex DNA by T4 Endo VII in wells of microtiter plates. Two different protocols were used to test binding of heteroduplex DNA by immobilized T4 Endo VII.
Figure 2B:
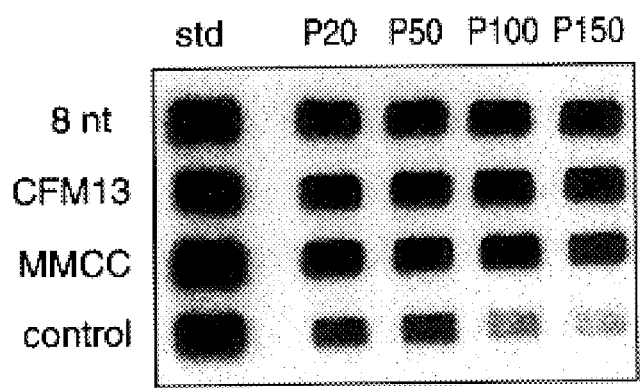
Figure 2C:
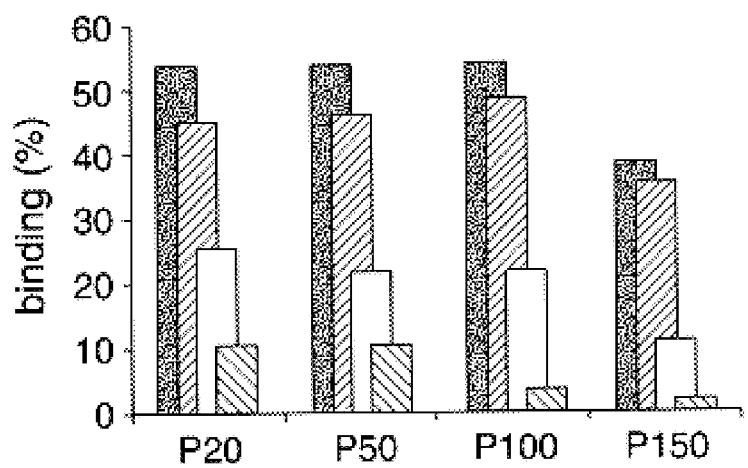

Results obtained with side by side trials of both protocols are shown in FIGS. 2A and 2B, and summarized for all substrates in FIG. 2C. It is evident that the amount of bound DNA was considerably higher when precoated microtiter wells were used (protocol II). The decreased efficiency of binding of preformed complexes was possibly a result of steric hindrance to the binding of the inner surface of the well. This was true for salt concentrations of 20 mM, 50 mM, 100 mM, and 150 mM. The largest difference between control and sample DNAs was seen when the binding reaction was performed with 150 mM phosphate buffer.

Use of a T4 Endo VII Cleavage Step

Figure 2D:
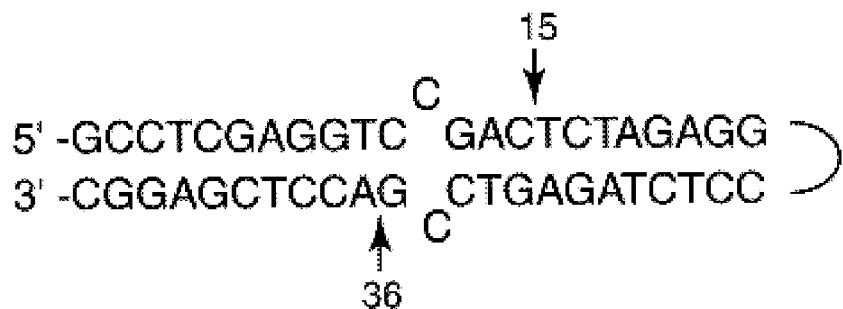
Figure 2E:
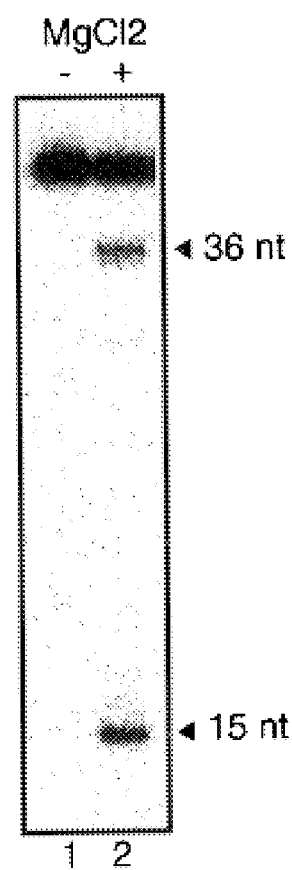

After identification of mismatch-containing samples using a binding assay (i.e., positive samples in any of the above binding techniques), the sample results may be checked by means of a resolvase cleavage assay. This second step can immediately follow the binding assay or can be carried out in parallel. For T4 Endo VII, this step involved the addition of $Mg^{2+}$ to an aliquot of the binding assay sample, or a duplicate sample. This addition of $Mg^{2+}$ triggered T4 Endo VII to cleave within a few nucleotides 3' of the mismatched nucleotide (FIG. 2D). In one particular example, an aliquot was taken from the sample indicated as "MMCC" in "P100" in FIG. 2B. This sample was treated with 15mM $Mg^{2+}$, incubated for 15 minutes at 37° C., and then electrophoresed through a 10% polyacrylamide (PAA) gel. The results, which are shown in FIG. 2E, demonstrate cleavage of the sample by T4 Endo VII upon $Mg^{2+}$ addition. In these experiments, an appropriate size marker allowed approximation of the fragment sizes, leading to the mapping of the location of the mutation as indicated in FIG. 2D.

Related Assay Techniques

Although the above techniques were carried out with T4 Endo VII, the general approach described herein may be utilized with other resolvases and with other reactive agents capable of both binding and cleaving a substrate under different reaction conditions. Additional embodiments of the invention are therefore set forth below.

i) Other reactive agents: Bacteriophage T4 endonuclease VII is one example of a resolvase known to bind and cleave DNA cruciforms under differing reaction conditions, and preferred methods for purifying this enzyme are presented, for example, in Babon et al., U.S. Ser. No. 08/545,404, hereby incorporated by reference. Additional resolvases with similar cleaving activity include bacteriophage T7 endonuclease I, and the S. cerevisiae cruciform cleaving enzymes Endo X1, Endo X2, Endo X3, and CCE1 (reviewed in West, S. C. supra). Methods for purifying bacteriophage T7 endonuclease I (deMassy, B., et al. J. Mol. Biol. 193: 359 (1987)), Endo XI (West, S. C. and Komer, A. PNAS, 82, 6445 (1985); (West, S.C. et al. J. Biol. Chem. 262: 12752 (1987)), Endo X2 (Symington, L.S. and Kolodner, R. PNAS 82: 7247 (1985)), Endo X3 (Jensch F. et al. EMBO J. 8, 4325 (1989)), and CCE1 (Kupfer and Kemper, Eur. J. Biochem. 238:77 (1995)) have been disclosed. The ability of each of these resolvases to bind at sites of mismatches may be examined using the assays described herein.

ii) Additional nucleic acid sequences: The techniques of the invention may be used to assay for a mismatched nucleic acid in a wide variety of different types of nucleic acid samples. For example, a DNA restriction fragment of known or unknown DNA sequence which is suspected of bearing at least one DNA mutation or polymorphism may be used as a test DNA in the formation of a heteroduplex. Preferably the DNA restriction fragment is at least 20 base pairs in length.

More preferably, the DNA restriction fragment is between 50 and 40,000 base pairs in length inclusive, most preferably between 100 and 5000 base pairs in length inclusive. In experiments where particularly large DNA fragments are analyzed (e.g., larger than 2 kb), it may be desirable to cleave the fragment with a second restriction enzyme to obtain a fragment of a size suitable for denaturing polyacrylamide gel electrophoresis (<2 kb). The choice of a second restriction enzyme will be guided by creating a restriction enzyme map of the fragment.

In another example, a DNA template for which at least a partial DNA sequence is known can be used as a source of amplified test DNA. Such amplification may be carried out by any known preparative technique, including PCR, NASBA, and SDA. Such amplification is performed by positioning primers on either side of a suspected mismatch or sequence of interest. If desired, these primers may be labeled, for example, with a radioactive or fluorescent label, or with biotin. In general, the amplified sequence will be at least 50 base pairs in length inclusive. Recent advances in PCR technology have allowed amplification of up to 40 kb of DNA. Preferably, the amplified region will be between 100 and 40,000 base pairs in length inclusive, more preferably between 150 and 5000 base pairs in length inclusive. Those skilled in the art will appreciate that where the flanking DNA sequence is only partially known, a degenerate DNA oligonucleotide primer may be used to prepare test DNA by PCR amplification.

In another example, duplex nucleic acid may be subdloned into a suitable cloning vector and amplified using known oligonucleotide primers which hybridize to the cloning vector and are adjacent to the insertion site of the template. In this instance, no template DNA sequence information is required because the DNA oligonucleotide primers used for PCR amplification hybridize to a vector of known DNA sequence and not the inserted template DNA. For example, the Bluescript™ vector can be used to sub-clone a DNA template into an acceptor site according to the manufacturer's instructions (Stratagene Cloning Systems, La Jolla, Calif., Product Catalogue, (1992)). The T7 and T3 DNA primers of the Bluescript vector can be used to PCR amplify the inserted DNA template (or concomitantly to sequence the inserted DNA template). Other commercially available sub-cloning vectors may also be used. These include, without limitation, phage lambda based insertion vectors and other prokaryotic and eukaryotic vectors (e.g., bacteriophage, insect virus (baculovirus), or animal virus (SV-40 or adenovirus) based vectors described by Stratagene supra, and Sambrook et al. supra). As described above, the PCR amplified DNA template may be used as a source of test DNA, or, in an alternative method, a vector which includes a DNA insert bearing at least one DNA mismatch may first be amplified by propagation in bacteria, phage, insect, or animal cells prior to PCR amplification (see Sambrook et al. supra). If sufficient DNA is available (i.e., at least 1 nanogram), the PCR amplification step can be eliminated.

In yet another example, RNA may be tested using the techniques described herein. the RNA may be purified from cells or tissues by techniques well known in the art. For example, RNA may be purified by olido-dT chromatography to prepare MRNA (see, for example, Sambrook et al., supra, and Ausubel et al., supra). In cases where ribosomal RNA is the subject of analysis or a particular MRNA is in abundance, oligo-dT chromatography will not be necessary. Purified RNA or mRNA is heat denatured to ensure complete single-strandedness and hybridized with a control strand (e.g., a control DNA strand) to form RNA:DNA heteroduplexes. Methods for forming RNA:DNA duplexes are well known in the art and have been described in detail (see Sambrook et al., supra). After formation of an RNA:DNA heteroduplex, the method described herein may be used to detect mismatches produced by mispairing between the DNA and the RNA. In preferred embodiments, the control DNA is 5' end-labeled. Alternatively, RNA can be uniformly labeled by adding radiolabeled uracil to living cells or tissues.

Either or both of the strands of the duplex nucleic acid may be derived from any eukaryotic cell (for example, a human cell), eubacterial cell, bacteriophage, DNA virus, or RNA virus. Preferred RNA viruses include, without limitation, human T-cell leukemia virus and human immunodeficiency virus (for example, HTLV-I, HTLV-II, HIV-1, and HIV-2). Preferred DNA viruses include, without limitation, any one of the family Adenoviridae, Papovaviridae, or Herpetoviridae. Preferred eubacterial cells include, without limitation, any member of the order Spirochaetales, Kinetoplastida, or Actinomycetales, of the family Treponemataceae, Trypoanosomatidae, or Mycobacteriaceae, and of the species *Mycobacterium tuberculosis, Treponema pallidum, Treponema pertenue, Borrelia burgdorferi,* or *Trypanosoma cruzi.*

The nucleic acid strands may also include any human gene that can act as the target of a therapeutic protein (for example, an essential human gene required for disease onset, maintenance, or progression), or a human gene involved in or diagnostic of a disease or condition, for example, an oncogene or a tumor suppressor gene; preferable mammalian oncogenes include, without limitation, abl, akt, crk, erb-A, erb-B, ets, fes/fps, fgr, fins, fos, jun, kit, mil/raf, mos, myb, myc, H-ras, K-ras, rel, ros, sea, sis, ski, src, and yes; preferable tumor suppressor genes include p53, retinoblastoma (preferably RB 1), adenomatous polyposis coli, NF-1, NF-2, MLH-1, MTS-1, MSH-2, BRCA-1, BRCA-2, ATM, and human non-polyposis genes.

Alternatively, one or both of the duplex nucleic acid strands may be isolated from any one of the β-globin, $\alpha_1$-antitrypsin, 21-hydroxylase, pyruvate dehydrogenase E1α-subunit, dihydropteridine reductase, rhodopsin, β-amyloid, nerve growth factor, superoxide dismutase, Huntington's disease, cystic fibrosis, adenosine deaminase, β-thalassemia, ornithine transcarbamylase, collagen, bcl-2, β-hexosaminidase, topoisomerase II, hypoxanthine phosphoribosyltransferase, phenylalanine 4-monooxygenase, Factor VIII, Factor IX, nucleoside phosphorylase, glucose-6-phosphate dehydrogenase, phosphoribosyltransferase, Duchenne muscular dystrophy, von Hippel Lindeau, or the mouse mottled Menkes genes. Nucleic acids may also be derived from any cell cycle control gene, preferably p21, p27, or p 16.

iii) Additional labeling techniques: The above-described methods may be carried out using any detectable label and any labeling technique. For example, the duplex nucleic acid may be 5' end-labeled or uniformly labeled with radioactive phosphorous either before or after heteroduplex formation. In one particular example, labeling may be carried out during PCR amplification using one or more deoxyribonucleotides (i.e., dNTPs: dA, dG, dC, or T) radiolabeled in the α position with radioactive phosphorus or sulfur (e.g. $^{32}$p, $^{33}$p, or $^{35}$S). In general, 0.1–50 μCi of one or more radioactively labeled dNTPs can be added to a PCR reaction and excess label removed by Sephadex G-50 column chromatography (for example, using a spin column). In another specific example, the duplex nucleic acid may be uniformly labeled during the PCR reaction using rhodamine-labeled uracil and standard techniques (Molecular Probes, Eugene, Oreg.). Alternatively, test duplexes can be tagged with biotin (Tizard et al. PNAS 87, 4514 (1990)) before or after heteroduplex formation. Methods for the detection of biotinylated DNA after polyacrylamide gel electrophoresis have been disclosed (Ausubel et al. supra Chapter 7). In one preferred embodiment, detection of a biotinylated duplex nucleic acid is accomplished by contacting the nucleic acid with a streptavidin-bound enzyme and a chromogenic substrate (for example, a horseradish peroxidase system). In yet another alternative method, duplex nucleic acids may be tagged with fluorescent dNTPs (for example, fluorescein; see, for example, Ansorge, W., et al. Nucl. Acids Res. 15, 4593 (1987); Johnston-Dow, E., et al. BioTechniques 5, 754 (1987); Prober, J., et al. Science 238, 336 (1987)). In yet another example, the 3'—>5' exonuclease activity of certain DNA polymerases, in particular T4 DNA polymerase, may be used to radiolabel heteroduplex DNA. Other labeling approaches are described in Cotton et al., U.S. Pat. No. 5,698,400, and Babon et al., U.S. Ser. No. 08/545,404, hereby incorporated by reference.

iv) Additional binding assays: The binding of a reactive agent to a duplex nucleic acid may be assayed by any known technique. For example, although the approach described above involves the detection of a labeled duplex nucleic acid captured by a reactive agent immobilized to a microtiter well, any other type of solid support may be utilized. Such solid supports include, without limitation, beads (for example, magnetic beads) as well as test tubes, plates, columns, or chips. Immobilization may also be accomplished by any appropriate means, including direct as well as indirect binding. Indirect binding may involve any type of covalent or non-covalent specific binding pair. Such binding pairs are well known in the art and include any pair involving nucleic acid or protein components that are not denatured or separated under the conditions employed in the assay; such pairs include, without limitation, antigen/antibody pairs, DNA binding protein/DNA binding site pairs (for example, the GCN4 protein and its DNA binding site), enzyme/substrate pairs, lectin/carbohydrate pairs, and base paired or ligated nucleic acids. A preferred specific binding pair according to the invention is avidin/biotin.

Alternatively, the binding reaction may be carried out in solution, and the complex detected by any standard technique. In one particular example, the complex may be isolated by capturing the duplex nucleic acid (for example, on a nitrocellulose filter) and assaying for the presence on the filter of bound, labeled reactive agent. Alternatively, the reactive agent may be captured (for example, by immunological techniques, such as immunoprecipitation or a specific antibody column), and the presence of labeled duplex nucleic acid assayed. In yet another approach, the reactive agent-duplex nucleic acid complex may be detected by standard techniques of DNA footprinting, gel retention assays, or other gel electrophoretic approaches.

v) Additional cleavage assays: As described above, the products of a mismatch cleavage reaction may be assayed by gel electrophoresis, preferably in the presence of size makers to determine the location of a mismatch in the duplex molecule. The present approach, however, is not limited to this technique, and may be carried out using any type of cleavage reaction and detection technique (for example, on a solid support). Examples of cleavage techniques useful in the invention are described in Cotton et al., U.S. Pat. No. 5,698,400, and Babon et al., U.S. Ser. No. 08/545,404, hereby incorporated by reference.

vi) Additional nucleic acid separation techniques: In addition to the well known basic denaturing polyacrylamide gel electrophoresis technique described above (see also Sambrook et al., supra), a variety of electrophoretic methods are available for increasing the resolution of reactive agent binding or cleavage products and in particular, for analyzing large cleavage products (e.g., >2 kb). Denaturing polyacrylamide gels exhibiting increased resolution have the advantage of allowing a more precise determination of the specific site of a mismatch in a duplex nucleic acid. Furthermore, such gels allow improved analysis of cleavage products. For example, wedge-shaped spacers may be used to create a field gradient or incorporate a buffer gradient, an electrolyte gradient, or an acrylamide step gradient. Formamide may be included in a standard denaturing polyacrylamide gel, or longer gels may also be employed (80 to 100 cm). These electrophoreic techniques have been described in detail (Ausubel et al., supra). Alternatively, cleavage products larger than 2kb can be specifically cut with a restriction enzyme to decrease fragment size, with the choice of a particular restriction enzyme being governed by a restriction enzyme map of the particular DNA to be analyzed. Alternatively, a large cleavage product can be electrophoresed on a denaturing (e.g., alkaline) agarose gel and directly visualized by reagents (e.g., stains or dyes) which interact with DNA, for example, silver, ethidium bromide, acridine orange, 4,6-diamidino-2-phenylindol (i.e. DAPI), Hoechst dyes, and the like (see Sambrook et al., supra; and Bassam et al., Anal. Biochem. 196, 80 (1991)). In addition, electrophoresed DNA may be transferred to a membrane (for example, DEAE-cellulose, nylon, or other suitable membranes) and visualized by filter hybridization with a radioactive or non-radioactive (e.g., biotin, digoxigenin, or fluorescein) tagged probe.

Alternatively, nucleic acids (for example, duplex nucleic acid cleavage products) may be separated by non-gel techniques including, without limitation, any HPLC column-based or capillary electrophoresis approach.

Other embodiments are within the claims.

What is claimed is:

1. A method for detecting a mismatch in a duplex nucleic acid, said method comprising:
   a) contacting said duplex nucleic acid with a resolvase which cleaves mismatches in duplex nucleic acids, under conditions which permit said resolvase to bind but not cleave said mismatch; and
   b) detecting said resolvase binding to said duplex nucleic acid as an indication of the presence of a mismatch in said duplex nucleic acid.

2. The method of claim 1, wherein said resolvase is a bacteriophage or a eukaryotic resolvase.

3. The method of claim 2, wherein said bacteriophage resolvase is T4 Endonuclease VII.

4. The method of claim 3, wherein said contacting occurs in the absence of magnesium.

5. The method of claim 1, wherein, prior to said contacting with said resolvase, said duplex nucleic acid is labeled with at least one detection moiety.

6. The method of claim 1, wherein between said contacting with said resolvase and said detection step said duplex nucleic acid is post-digestion labeled with at least one detection moiety.

7. The method of claim 5 or 6, wherein said detection moiety is any one of a radioactive label, a fluorescent label, biotin, digoxygenin, a luminescent agent, a dye, or an enzyme.

8. The method of claim 1, wherein at least one strand of said duplex is labeled with biotin and said detecting step comprises reaction of said duplex with a streptavidin-bound detection moiety.

9. The method of claim 8, wherein said streptavidin-bound detection moiety is an enzyme which produces a detectable color upon reaction with a chromogenic substrate.

10. The method of claim 1, wherein at least one strand of said duplex nucleic acid is provided by amplification.

11. The method of claim 1, wherein said resolvase or said duplex nucleic acid is bound to a solid support.

12. The method of claim 11, wherein said resolvase is bound to said solid support.

13. The method of claim 11, wherein said solid support is a microtiter plate or a magnetic bead.

14. The method of claim 1, wherein said contacting step is carried out in solution.

15. The method of claim 1, wherein the site of said resolvase binding is determined.

16. The method of claim 1, further comprising the steps of:
   c) contacting said duplex nucleic acid with said resolvase under conditions which permit said resolvase to cleave a mismatch in said duplex nucleic acid; and
   d) detecting a cleavage product as an indication of the presence of a mismatch in said duplex nucleic acid.

17. The method of claim 16, wherein said resolvase cleaves at or within 10 nucleotides of said mismatch.

18. The method of claim 16, wherein the site of said resolvase cleavage reaction is determined.

19. The method of claim 1, wherein said duplex nucleic acid is obtained from a heterozygote.

20. The method of claim 1, wherein at least one strand of said duplex nucleic acid is obtained from a eukaryotic cell, a eubacterial cell, a bacterial cell, a mycobacterial cell, a bacteriophage, a DNA virus, or an RNA virus.

21. The method of claim 20, wherein at least one strand of said duplex nucleic acid is obtained from a human cell.

22. The method of claim 1, wherein said duplex nucleic acid comprises at least one strand having a wild-type sequence.

23. The method of claim 1, wherein said mismatch indicates the presence of a mutation.

24. The method of claim 23, wherein said mutation is diagnostic of a disease or condition.

25. The method of claim 1, wherein said mismatch indicates the presence of a polymorphism.

26. The method of claim 1, wherein said mismatch occurs in an essential gene.

27. A method for detecting a mismatch in a duplex nucleic acid, said method comprising:
   a) contacting said duplex nucleic acid with a reactive agent under conditions which permit said agent to bind but not cleave a mismatch in said duplex nucleic acid;
   b) detecting binding of said agent to said duplex nucleic acid as an indication of the presence of a mismatch in said duplex nucleic acid;
   c) contacting said duplex nucleic acid with said reactive agent under conditions which permit said agent to cleave a mismatch in said duplex nucleic acid; and
   d) detecting a cleavage product as an indication of the presence of a mismatch in said duplex nucleic acid.

28. The method of claim 27, wherein said binding and said cleaving are carried out on the same sample.

29. The method of claim 27, wherein said binding and said cleaving are carried out on separate samples of the same duplex nucleic acid.

30. The method of claim 27, wherein said reactive agent is T4 Endonuclease VII.

31. The method of claim 30, wherein said binding occurs in the absence of magnesium and said cleaving occurs in the presence of magnesium.

32. The method of claim 27, wherein, prior to said contacting with said reactive agent, said duplex nucleic acid is labeled with at least one detection moiety.

33. The method of claim 27, wherein, between said contacting with said reactive agent and said detection step (b) or (d), said duplex nucleic acid is post-digestion labeled with at least one detection moiety.

34. The method of claim 32 or 33, wherein said detection moiety is any one of a radioactive label, a fluorescent label, biotin, digoxygenin, a luminescent agent, a dye, or an enzyme.

35. The method of claim 27, wherein at least one strand of said duplex is labeled with biotin and said detecting step (b) and/or (d) comprises reaction of said duplex with a streptavidin-bound detection moiety.

36. The method of claim 35, wherein said streptavidin-bound detection moiety is an enzyme which produces a detectable color upon reaction with a chromogenic substrate.

37. The method of claim 27, wherein at least one strand of said duplex nucleic acid is provided by amplification.

38. The method of claim 27, wherein said reactive agent is bound to a solid support during said detecting step (b).

39. The method of claim 38, wherein said solid support is a microtiter plate or a magnetic bead.

40. The method of claim 27, wherein said binding, said cleaving, or both is carried out in solution.

41. The method of claim 27, wherein the site of said mismatch is determined in step (b), step (d), or both.

42. The method of claim 27, wherein said reactive agent cleaves at or within 10 nucleotides of said mismatch.

43. The method of claim 27, wherein said duplex nucleic acid is obtained from a heterozygote.

44. The method of claim 27, wherein at least one strand of said duplex nucleic acid is obtained from a eukaryotic cell, a eubacterial cell, a bacterial cell, a mycobacterial cell, a bacteriophage, a DNA virus, or an RNA virus.

45. The method of claim 44, wherein at least one strand of said duplex nucleic acid is obtained from a human cell.

46. The method of claim 27, wherein said duplex nucleic acid comprises at least one strand having a wild-type sequence.

47. The method of claim 27, wherein said mismatch indicates the presence of a mutation.

48. The method of claim 47, wherein said mutation is diagnostic of a disease or condition.

49. The method of claim 27, wherein said mismatch indicates the presence of a polymorphism.

50. The method of claim 27, wherein said mismatch occurs in an essential gene.

* * * * *

UNITED STATES PATENT AND TRADEMARK OFFICE
CERTIFICATE OF CORRECTION

PATENT NO.    : 6,110,684
DATED         : August 29, 2000
INVENTOR(S)   : Kemper et al.

It is certified that error appears in the above-identified patent and that said Letters Patent is hereby corrected as shown below:

Title page,
Item [75], Inventors, replace "Karin Birkenkamp-Demtröder, Solingen;" with
-- Karin Birkenkamp-Demtröder, Ugelbolle Denmark; --; remove "all of Germany".
Item [56], References Cited, OTHER PUBLICATIONS, "Forrest et al." reference, replace ")1992)." with -- (1992). --.
"Kosak et al." reference, replace "rrom" with -- from --.

Column 6,
Line 57, replace "100 pl" with -- 100 $\mu$l --.

Column 7,
Line 45, replace "1 5mM" with -- 15mM --.

Column 8,
Line 11, replace "Fg/ml" with -- $\mu$g/ml --.
Line 50, replace "1 64bp" with -- 164bp --.

Column 9,
Line 51, replace "CFM113" with -- CFM13 --.

Column 10,
Line 50, replace "Komer" with -- Korner --.

Column 11,
Lines 60 and 62, replace "MRNA" with -- mRNA --; and

UNITED STATES PATENT AND TRADEMARK OFFICE
CERTIFICATE OF CORRECTION

PATENT NO. : 6,110,684
DATED : August 29, 2000
INVENTOR(S) : Kemper et al.

It is certified that error appears in the above-identified patent and that said Letters Patent is hereby corrected as shown below:

Column 12,
Line 29, replace "fins" with -- fms --;
Line 32, replace "RB 1" with -- RB1 --;
Line 48, replace "p 16" with -- p16 --; and
Line 58, replace "$^{32}$p $^{33}$p," with -- $^{32}$P, $^{33}$P, --.

Signed and Sealed this

Twenty-eighth Day of June, 2005

JON W. DUDAS
*Director of the United States Patent and Trademark Office*

SEQUENCE LISTING

<160> NUMBER OF SEQ ID NOS: 1

<210> SEQ ID NO 1
<211> LENGTH: 46
<212> TYPE: DNA
<213> ORGANISM: Artificial Sequence -continued

```
<220> FEATURE:
<223> OTHER INFORMATION: Heteroduplex hairpin

<400> SEQUENCE: 1
gcctcgaggt ccgactctag aggcctctag agtccgacct cgaggc        46
```